United States Patent
Itoh

(10) Patent No.: US 9,016,743 B2
(45) Date of Patent: Apr. 28, 2015

(54) CHUCKING APPARATUS

(71) Applicant: AOI Seiki, Co., Ltd., Kumamoto-shi, Kumamoto-ken (JP)

(72) Inventor: Teruaki Itoh, Kumamoto (JP)

(73) Assignee: Aoi Seiki Co., Ltd., Kumamoto (JP)

( * ) Notice: Subject to any disclaimer, the term of this patent is extended or adjusted under 35 U.S.C. 154(b) by 0 days.

(21) Appl. No.: 14/066,878

(22) Filed: Oct. 30, 2013

(65) Prior Publication Data
US 2014/0117690 A1    May 1, 2014

(30) Foreign Application Priority Data
Oct. 30, 2012   (JP) .................................. 2012-239391

(51) Int. Cl.
| | |
|---|---|
| B66C 1/00 | (2006.01) |
| B66C 1/42 | (2006.01) |
| B25J 15/02 | (2006.01) |
| B25J 15/00 | (2006.01) |
| H02P 4/00 | (2006.01) |
| B65G 47/90 | (2006.01) |
| G01N 35/00 | (2006.01) |

(52) U.S. Cl.
CPC .......... *B25J 15/0206* (2013.01); *B25J 15/0028* (2013.01); *H02P 4/00* (2013.01); *B65G 47/905* (2013.01); *G01N 35/0099* (2013.01); *Y10S 294/907* (2013.01)

(58) Field of Classification Search
CPC ........ B25B 5/122; B25B 5/061; B25B 5/087; B25B 5/16; B25B 1/18; B25B 9/00; B25J 9/041; B25J 9/1697; H01L 21/68707; B23Q 7/04; B66F 9/181; B66F 9/18; Y10S 294/902; Y10S 294/907; Y10S 901/47; B66C 1/422; B65G 47/90; G05D 1/0272; G05D 1/0242
USPC ............ 294/106, 94, 198, 902, 907, 87.1, 95, 294/115–116, 119.1, 192, 203, 207; 901/39, 37, 46–47; 269/32, 34; 414/618, 744.8
See application file for complete search history.

(56) References Cited

U.S. PATENT DOCUMENTS

| | | | |
|---|---|---|---|
| 5,102,287 A * | 4/1992 | Johnson et al. | 414/618 |
| 5,538,305 A * | 7/1996 | Conway et al. | 294/119.1 |
| 6,257,636 B1 * | 7/2001 | Hovis et al. | 294/110.1 |
| 6,264,419 B1 * | 7/2001 | Schinzel | 414/751.1 |

(Continued)

FOREIGN PATENT DOCUMENTS

| | | |
|---|---|---|
| JP | 5-136254 | 6/1993 |
| JP | 5-341827 | 12/1993 |

(Continued)

OTHER PUBLICATIONS

Extended European Search Report in EP 13 00 5110 dated Jan. 13, 2014.
Korean Official Action and English language translation in KR 2013-0129316 mailed Oct. 1, 2014.

*Primary Examiner* — Stephen Vu
(74) *Attorney, Agent, or Firm* — Nixon & Vanderhye P.C.

(57) ABSTRACT

According to one embodiment, A chucking apparatus includes an arm that is configured to hold a test tube, an opening/closing mechanism that opens/closes the arm, a motor that drives the opening/closing mechanism, and a supplying unit configured to supply electric power to the motor at two different supply voltages.

2 Claims, 2 Drawing Sheets

(56) References Cited

U.S. PATENT DOCUMENTS

| | | | |
|---|---|---|---|
| 6,435,582 B1 * | 8/2002 | DaSilva et al. | 294/94 |
| 6,652,015 B1 * | 11/2003 | Carney et al. | 294/86.4 |
| 7,261,352 B2 | 8/2007 | Maslov et al. | |
| 8,267,451 B2 * | 9/2012 | Pedrazzini | 294/207 |
| 2004/0074320 A1 | 4/2004 | Itoh | |

FOREIGN PATENT DOCUMENTS

| | | |
|---|---|---|
| JP | 9-86859 | 3/1997 |
| JP | 2000 051514 A | 2/2000 |
| JP | 2011-13086 | 1/2011 |

\* cited by examiner

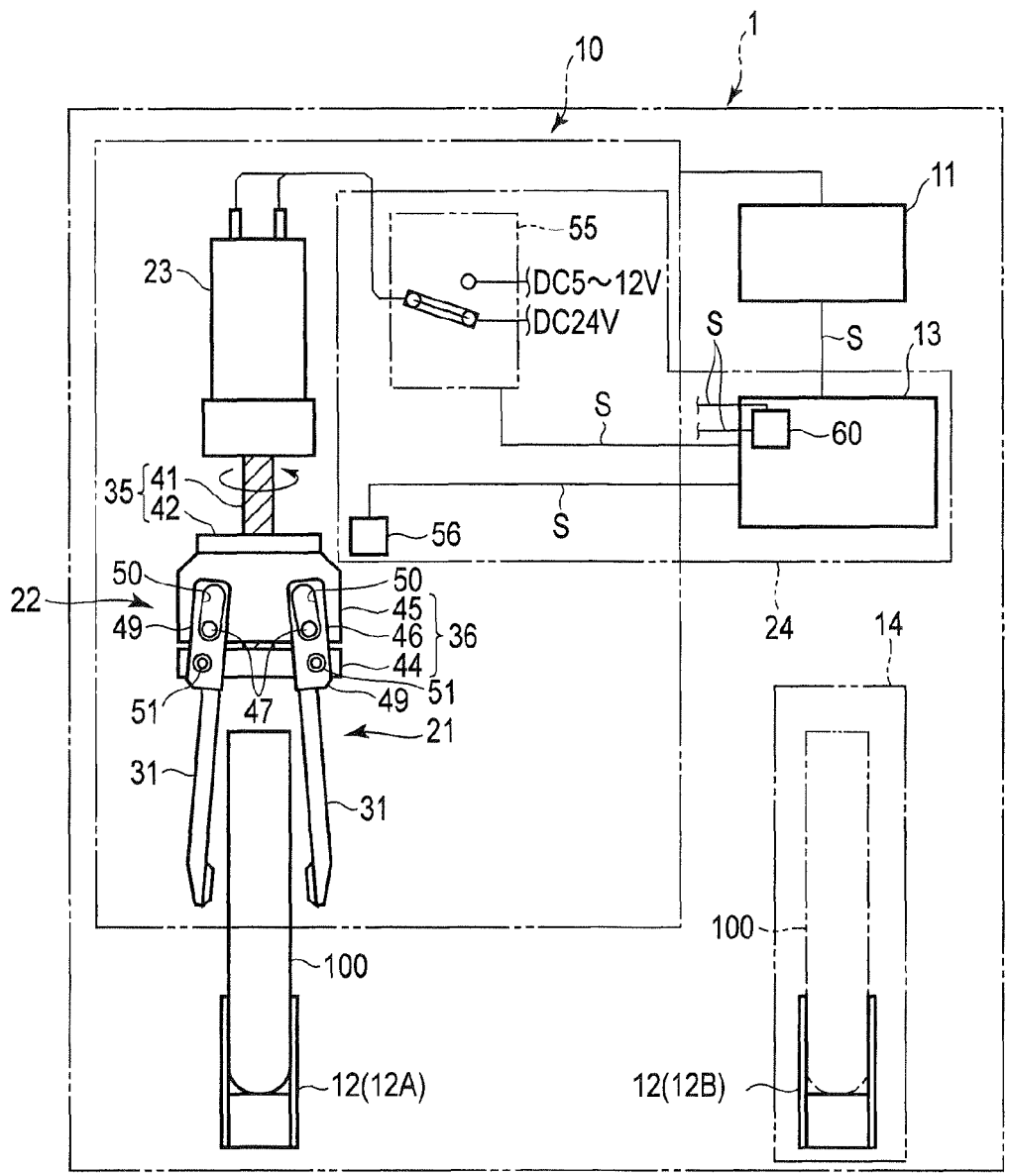
F I G. 1

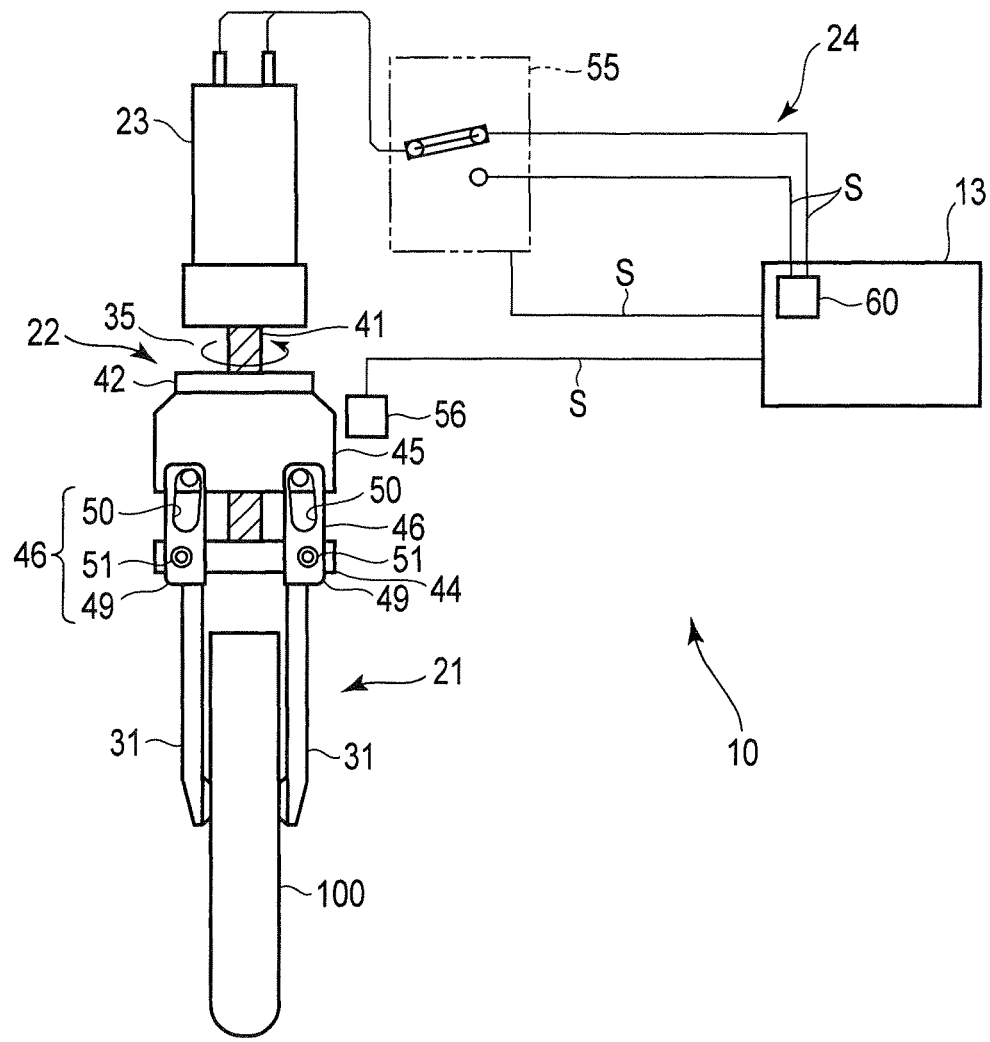
F I G. 2

CHUCKING APPARATUS

CROSS-REFERENCE TO RELATED APPLICATIONS

This application is based upon and claims the benefit of priority from prior Japanese Patent Application No. 2012-239391, filed Oct. 30, 2012, the entire contents of which are incorporated herein by reference.

BACKGROUND OF THE INVENTION

1. Field of the Invention

The present invention relates to a chucking apparatus that holds a test tube.

2. Description of the Related Art

At present, in Jpn. Pat. Appln. KOKAI Publication No. 2011-13086, a specimen treatment apparatus is known which carries a specimen such as blood in a state where the specimen is accommodated in a test tube, and gives various kinds of treatments. The specimen treatment apparatus holds the test tube by a chucking apparatus, moves the chucking apparatus by a moving apparatus to a position where the treatment is given, and releases a held state of the test tube by the chucking apparatus. Through such a process, the specimen treatment apparatus carries the test tube to a predetermined position.

Such a chucking apparatus comprises an arm that holds the test tube by nipping the same, an opening/closing mechanism that opens or closes the arm, and a driving unit having an air compressor and an air cylinder that drive the opening/closing mechanism. After holding the test tube by the arm, the chucking apparatus continuously drives the opening/closing mechanism by the driving unit while the test tube is carried to a predetermined position by the moving apparatus, whereby the holding of the test tube by the arm is maintained.

The above-described chucking apparatus has the following problem. That is, the chucking apparatus is configured to drive the opening/closing mechanism by the driving unit using the air compressor and the air cylinder, and hence it has a problem that a size of the apparatus itself increases.

For example, it can be contrived that the air compressor and the air cylinder are not used for the driving unit and a motor is instead used for the driving unit. However, when the motor is used, supply of electric power to the motor must be continued to maintain a held state after the test tube is held by the arm, with the result that the motor may be possibly damaged due to heat generation or overcurrent of the motor.

BRIEF SUMMARY OF THE INVENTION

According to an aspect of the present invention, there is provided a chucking apparatus including an arm that is configured to hold a test tube, an opening/closing mechanism that opens/closes the arm, a motor that drives the opening/closing mechanism, and a supplying unit configured to supply electric power to the motor at two different supply voltages.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is an explanatory view showing a configuration of a specimen treatment apparatus according to an embodiment of the present invention; and FIG. 2 is an explanatory view showing a configuration of a chucking apparatus used in the specimen treatment apparatus.

DETAILED DESCRIPTION OF THE INVENTION

A configuration of a chucking apparatus 10 used in a specimen treatment apparatus 1 according to an embodiment of the present invention will now be described with reference to FIG. 1 and FIG. 2.

FIG. 1 is an explanatory view schematically showing a configuration of the specimen treatment apparatus 1 according to an embodiment of the present invention, and FIG. 2 is an explanatory view schematically showing an example of use of a configuration of the chucking apparatus 10 adopted in the specimen treatment apparatus 1.

As shown in FIG. 1, the specimen treatment apparatus 1 comprises the chucking apparatus 10 that holds a test tube 100; a moving apparatus 11 that moves the chucking apparatus 10, a plurality of test tube holders 12 each supporting the test tube 100, and a control apparatus 13. Further, the specimen treatment apparatus 1 comprises a treatment unit 14 for giving a specimen accommodated in the test tube a treatment.

Such a specimen treatment apparatus 1 is formed to carry the test tube 100 to a position, at which a treatment is given to a specimen by the treatment unit 14, by using the chucking apparatus 10 and the moving apparatus 11 so that the treatment can be given to the specimen.

The test tube 100 is formed to accommodate the specimen therein. As the test tube 100, although the cylindrical configuration having a dome-like bottom portion will be described in FIG. 1, the present invention is not restricted thereto, and it is possible to adopt any other configuration that can accommodate the specimen and can be held by the chucking apparatus 10.

The chucking apparatus 10 comprises an arm 21, an opening/closing mechanism 22, a motor 23, and a supplying unit 24.

The arm 21 is constituted of a pair of arm portions 31. The arm 21 is configured in such a manner that ends of the pair of arm portions 31 can be opened/closed. Here, the opening/closing of the ends of the pair of arm portions 31 means that the pair of arm portions 31 move closer to or away from each other. The arm 21 pinches and holds the test tube 100 when the pair of arm portions 31 are closed.

The opening/closing mechanism 22 is formed to enable opening/closing the end of the arm 21. Specifically, the opening/closing mechanism 22 comprises a conversion mechanism 35 that converts a rotational movement of the motor 23 into a linear movement and a link mechanism 36 that opens or closes the arm 21 by the linear movement.

The conversion mechanism 35 comprises a ball screw 41 connected to a rotary shaft of the motor 23 and a ball nut 42 screwed with respect to the ball screw 41. In the ball nut 42, movement of the ball screw 41 in a rotating direction is restricted.

The link mechanism 36 comprises a base portion 44, a movable portion 45, and a link 46. The base portion 44 is rotatably fixed to an end of the ball screw 41. In other words, the base portion 44 is fixed to the end of the ball screw 41 and pivotally supports the ball screw 41 in a rotatable manner.

The movable portion 45 is fixed to the ball nut 42 and formed to be movable in accordance with movement of the ball nut 42. The movable portion 45 comprises a pair of pins 47.

The link 46 comprises a pair of link portions 49 each of which is formed into a long plate shape, groove portions 50 which are formed in the respective link portions 49 and in which the pins 47 are slid, and rotary shafts 51 fixed to the base portion 44. Each arm portion 31 is fixed to one end of each link portion 49, and the groove portion 50 is formed to the other end side of the same. Further, the rotary shaft 51 is provided between one end portion of the link portion 49 and the groove portion 50, and the link portion 49 revolves around the rotary shaft 51.

Each groove portion 50 is extended so that each pin 47 can linearly move therein. The groove portion 50 is formed in the link portion 49 in such a manner that its longitudinal direction is inclined with respect to a moving direction of the movable portion 45 when each link portion 49 is fixed to the base portion 44 through the rotary shaft 51. In other words, each groove portion 50 is formed to enable a removing motion of each link portion 49 around the rotary shaft 51 when each pin 47 linearly moves with the movement of the movable portion 45.

For example, a shape of each groove portion 50 is formed in such a manner that the ends of the pair of link portions 49 are moved away from each other and the pair of arm portions 31 are opened when the movable portion 45 moves closer to the base portion 44. Furthermore, for example, the shape of each groove portion 50 is formed in such a manner that the ends of the pair of link portions 49 move closer to each other and the pair of arm portions 31 are closed when the movable portion 45 moves away from the base portion 44.

The motor 23 is a DC motor. The motor 23 is formed to enable rotating the ball screw 41. The motor 23 is formed to have a rated voltage of, e.g., 24 V. The motor 23 is formed to enable switching a rotating direction of the ball screw 41 by changing over a flow direction of a current thereof.

The supplying unit 24 is connected to the motor 23 and a supply source of electric power and formed to enable supplying the electric power from the supply source to the motor 23. Specifically, the supplying unit 24 is configured to supply, to the motor 23, one of two types of electric power set to two different supply voltages. The supplying unit 24 is constituted of a switching relay 55, a detector 56, and a control apparatus 13.

The switching relay 55 is also a switching unit configured to enable switching electric power that is supplied to the motor 23. For example, the two different supply voltages are the rated voltage of the motor 23 and a low voltage which is lower than this rated voltage. For example, the rated voltage is 24 V, and the low voltage is 5 V to 12 V. Here, the low voltage can be appropriately set as long as it is a voltage that can decrease a load of the motor 23 and enable the pair of arm portions 31 to pinch the test tube 100.

The switching relay 55 is electrically connected to the control apparatus 13 through a signal line S and configured to enable switching a flow of a current by using the control apparatus 13. The switching relay 55 is connected through the signal line S to a supply source to which the rated voltage is supplied, e.g., a supply source 60 that is formed in the control apparatus 13 and supplies the rated voltage. Moreover, in a second state switched from a first state, the switching relay 55 is connected through the signal line S to a supply source to which the low voltage is supplied, e.g., the supply source 60 that is formed in the control apparatus 13 and supplies the low voltage.

The detector 56 is formed to enable detecting a held state of the test tube 100 by the arm 21. For example, the detector 56 is formed to enable detecting the movable portion 45 placed at a position where the pair of arm portions 31 connected to the link portions 49 can hold the test tube 100. The detector 56 is connected to the control apparatus 13 through the signal line S. The detector 56 is formed to enable transmitting detected information of the movable portion 45 to the control apparatus 13.

The moving apparatus 11 is configured to enable moving the chucking apparatus 10. For example, the moving apparatus 11 is formed to enable moving the chucking apparatus 10 in three axis directions. The moving apparatus 11 is connected to the control apparatus 13 through the signal line S.

The plurality of test tube holders 12 are provided. Each test tube holder 12 is formed so that it can support the test tube 100. For example, the test tube holders 12 include a test tube holder 12A provided at a first position at which the test tube 100 is taken out and a test tube holder 12B provided at a second position to which the test tube 100 is carried to be processed by, e.g., the treatment unit 14.

The control apparatus 13 is electrically connected to the moving apparatus 11, the switching relay 55, and the detector 56 through the signal line S. The control apparatus 13 is formed to enable supplying electric power to the motor 23. The control apparatus 13 has the supply source 60 that supplies electric power to the motor 23 at, e.g., two different supply voltages. The switch relay 55 is connected to the supply source 60, and one of a rated voltage and a low voltage is supplied to the motor 23 in accordance with a state of the switching relay 55. Furthermore, the control apparatus 13 is formed to enable changing over the switching relay 55 based on a detection result detected by the detector 56.

The control apparatus 13 is configured to move the chucking apparatus 10 to the test tube 100 to be held by controlling the moving apparatus 11 and moving the chucking apparatus 10. Further, the control apparatus 13 is configured to carry the test tube 100 held by the chucking apparatus 10 to a predetermined position by moving the chucking apparatus 10.

The carriage of the test tube 100 performed by the thus configured specimen treatment apparatus 1 will now be described. In this embodiment, a description will be given as to a configuration where the test tube 100 is moved from the first position 12A corresponding to the test tube holder 12A to the second position 12B corresponding to the test tube holder 12B.

First, when the control apparatus 13 receives an instruction to carry the test tube 100 from the first position 12A to the second position 12B from, e.g., an external input or a program stored in advance, the control apparatus 13 controls the moving apparatus 11 and moves the chucking apparatus 10 to the upper side of the first position 12A.

Then, the control apparatus 13 opens the pair of arm portions 31 and places the test tube 100 between the pair of arm portions 31. Specifically, the control apparatus 13 supplies electric power to the motor 23 through the switching relay 55 by using a rated voltage and opens the ends of the pair of arm portions 31. It is to be noted that the control apparatus 13 rotates the motor 23 in a rotating direction of the ball screw 41 moving in a direction along which the ball nut 42 moves close to the base portion 44 at this time. Furthermore, the control apparatus 13 controls the moving apparatus 11 so that the ends of the pair of arm portions 31 can be placed in a middle portion of the test tube 100, and it moves down the chucking apparatus 10.

The control apparatus 13 moves down the chucking apparatus 10 to a position where the test tube 100 can be held and then supplies electric portion to the motor 23, thereby holding the test tube 100 by the pair of arm portions 31. Specifically, as shown in FIG. 1, the control apparatus 13 supplies the electric power to the motor 23 by using the rated voltage. It is to be noted that the control apparatus 13 rotates the motor 23 in a rotating direction of the ball screw 41 along which the ball nut 42 moves away from the base portion 44.

In the chucking apparatus 10, the ball screw 41 rotates by the rotation of the motor 23, and the ball nut 42 moves. As a result, the movable portion 45 moves in the direction to get away from the base portion 44. With the movement of the movable portion 45, the pins 47 also linearly move. When the pins 47 move in the groove portions 50 of the link portions 49, the groove portions 50 are pressed by the pins 47, and the link portions 49 revolve around the rotary shafts 51 in a direction along which the ends thereof move closer to each other.

With the movement of the link portions 49, the ends of the pair of arm portions 31 move close to each other. As a result, the arm portions 31 are closed and pinch the test tube 100. When the detector 56 detects that the movable portion 45 has been placed at a position where the pair of arm portions 31 can hold the test tube 100, it transmits information of this detection to the control apparatus 13.

Upon receiving the information from the detector 56, the control apparatus 13 changes over the switching relay 55 as shown in FIG. 2 and supplies the electric power of the low voltage lower than the rated voltage to the motor 23. As a result, in a state that an output from the motor 23 is lowered, i.e., a state that the nipping force is lowered, the pair of arm portions 31 maintain holding the test tube 100.

In this state, the control apparatus 13 controls the moving apparatus 11 and carries the test tube 100 from the test tube holder 12A which is the first position 12A to the test tube holder 12B which is the second position 12B. After the carriage of the test tube 100 to the test tube holder 12B, the control apparatus 13 supplies the electric power to the motor 23 by using the rated voltage. It is to be noted that, at this moment, the control apparatus 13 changes the rotating direction of the motor 23 so that the movable portion 45 can move closer to the base portion 44.

As a result, the held state of the test tube 100 by the chucking apparatus 10 is released, and the test tube 100 is supported by the test tube holder 12B. The control apparatus 13 controls the moving apparatus 11 and moves the chucking apparatus 10 away from the test tube 100. In this manner, the specimen treatment apparatus 1 carries the test tube 100. Moreover, the specimen treatment apparatus 1 gives a specimen a treatment by using the treatment unit 14.

According to the thus configured specimen treatment apparatus 1, after the detector 56 detects that the test tube 100 is held by the arm 21, the chucking apparatus 10 decreases the supply voltage of the electric power that is supplied to the motor 23 by changing over the switching relay 55. When the low voltage is applied to the motor 23 while the chucking apparatus 10 maintains the held state of the test tube 100 in the arm 21, a load of the motor 23 can be reduced. As a result, an excessive load or current can be prevented from being applied to the motor 23, and heat generation of the motor 23 and damage to the motor due to overcurrent can be avoided.

As described above, according to the specimen treatment apparatus 1 based on one embodiment of the present invention, after the test tube 100 is held, the load of the motor 23 can be reduced by lowering the supply voltage used for driving the motor 23, and the held state of the test tube 100 can be maintained even if the motor 23 is used.

It is to be noted that the present invention is not restricted to the foregoing embodiment. In the above-described example, the description has been given as to the configuration that the chucking apparatus 10 is used for the specimen treatment apparatus 1, but the present invention is not restricted thereto. The chucking apparatus may be configured to be used for a carriage apparatus that performs carriage of the test tube 100 alone without giving a specimen a treatment. Although the description has been given as to the configuration of the chucking apparatus 10 that the arm 21 is opened or closed by the conversion mechanism 35 and the link mechanism 36, but the present invention is not restricted thereto. Any other configuration of the chucking apparatus 10 can be adopted as long as it is a configuration that the arm 21 is opened/closed by power of the motor 23 and the supply of the electric power to the motor 23 is maintained while the held state of the test tube 100 by the arm 21 is maintained.

Moreover, in the foregoing example, although the description has been given as to the configuration of the specimen treatment apparatus 1 that the test tube 100 accommodating a specimen is carried by the chucking apparatus 10 and the moving apparatus 11 to the position where a treatment is given to the specimen, the present invention is not restricted thereto. For example, it is possible to adopt a configuration that the test tube 100 having no specimen accommodated therein is carried by the chucking apparatus 10 and the moving apparatus 11.

Additionally, although the description has been given as to the configuration that the control apparatus 13 has the supply source 60 that supplies the electric power to the motor 23 at two different supply voltages, the present invention is not restricted thereto. The supply source 60 may be provided separately from the control apparatus 13 as long as it can supply two different voltages to the motor 23.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. A chucking apparatus comprising:
 an arm that is configured to hold a test tube;
 an opening/closing mechanism that opens/closes the arm;
 a motor that drives the opening/closing mechanism; and
 a supplying unit comprising a detector configured to detect a held state of the test tube by the arm;
 a switching unit configured to switch to one of two different supply voltages; and
 a control device which changes over the switching unit and decreases the supply voltage of the electric power supplied to the motor after the detector has detected the held state of the test tube, the supply unit configured to supply electric power to the motor at the two different supply voltages.
2. The apparatus according to claim 1,
 wherein one of the two different supply voltages is a rated voltage of the motor, and the other of the two different supply voltages is a voltage lower than the rated voltage.

* * * * *